United States Patent [19]

Duffett

[11] Patent Number: Plant 5,353

[45] Date of Patent: Nov. 20, 1984

[54] CHRYSANTHEMUM PLANT NAMED VISTA

[75] Inventor: William E. Duffett, Salinas, Calif.

[73] Assignee: Yoder Brothers, Inc., Barberton, Ohio

[21] Appl. No.: 472,645

[22] Filed: Mar. 7, 1983

[51] Int. Cl.[3] ..... A01H 5/00

[52] U.S. Cl. ..... Plt./78

[58] Field of Search ..... Plt./74, 78

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Vista having semi-incurved to flat capitulum form; anemone capitulum type; light bronze to golden yellow ray floret color; diameter across face of capitulum ranging from 35 to 50 mm. at maturity; uniform seven week photoperiodic flowering response to short days; short plant height when grown as a pinched spray pot mum, and spreading branching pattern.

3 Drawing Figures

The present invention comprises a new and distinct cultivar of *Chrysanthemum morifolium*, Ramat., named Vista.

Vista is a product of a planned breeding program which had the objective of creating new chrysanthemum cultivars for pinched, spray pot mum programs having anemone capitulum type, a yellow ray floret color, seven to eight week flowering response, and the ability to produce commercially acceptable quality in year round programs. Such traits in combination were not present or required improvement in previously available commercial cultivars.

Vista was originated from a cross made in a controlled breeding program in Salinas, Calif. in 1978. The female parent was Russet, disclosed in pending application Ser. No. 337,724 and originated by the present inventor from a hybridization of an unnamed yellow anemone seedling (Illini #73-99) and an unnamed color intensification mutant of the cultivar Fiesta, disclosed in U.S. Plant Pat. No. 3,632. The male parent of Vista was an unnamed bronze daisy seedling originated from a cross between an unnamed bronze daisy seedling and Circus, disclosed in U.S. Plant Pat. No. 4,118.

Vista was discovered and selected as one flowering plant within the progeny of the stated cross by William E. Duffett in December 1979 in a controlled environment in Salinas, Calif.

The first act of asexual reproduction of Vista was accomplished when vegetative cuttings were taken from the initial selection in April 1980 in a controlled environment in Salinas, Calif. by a technician working under formulations established and supervised by William E. Duffett. Horticultural examination of selected units initiated Apr. 4, 1981 has demonstrated that the combination of characteristics as herein disclosed for Vista are firmly fixed and are retained through successive generation of asexual reproduction.

Vista has not been observed under all possible environmental conditions. The phenotype may vary significantly with variations in environment such as temperature, light intensity and day length. The observations, measurements and comparisons describe plants grown in Salinas, Calif. and Leamington, Canada under greenhouse conditions which approximate those generally used in commercial practice.

The following traits have been repeatedly observed and are determined to be basic characteristics of Vista which in combination distinguish this chrysanthemum as a new and distinct cultivar;

(1) semi-incurved to flat capitulum form;

(2) Anemone capitulum type;

(3) Light bronze to golden yellow ray floret color;

(4) Diameter across face of capitulum ranging from 35 to 50 mm. at maturity;

(5) Uniform seven weeks photoperiodic flowering response to short days;

(6) Short Plant Height, requiring 2-3 long day weeks prior to pinch and short days, and 0-1 applications of 2500 ppm B-9 after the beginning of short days to attain a flowered plant height of 20 to 30 cm, and (7) Spreading branching pattern.

The accompanying photographic drawings depict typical foliage and inflorescence characteristics of Vista. Sheet 1 is a color photograph of a plant of Vista grown as a pinched spray pot mum, with colors being as accurate as possible with renditions of this type. Sheet 2 is a black and white photograph of three views of the inflorescence of Vista. Sheet 3 shows the leaves of Vista in three stages of development (mature, intermediate, immature).

Of the many commercial cultivars known to the present inventor, the most similar in comparison to Vista is Ritz, disclosed in U.S. Plant Pat. No. 3,863. Reference is made to attached Chart A which compares certain characteristics of Vista to those same characteristics of Ritz.

Vista is similar to Ritz in its use as a spray pot mum and its yellow color.

Vista differs from Ritz in capitulum form and type, and has a more spreading branching habit, smaller capitulum diameter and 7 versus 9 week flowering response period.

In the following description, color references are made to The Royal Horticultural Society Colour Chart. The color values were determined between 1:30 P.M. and 2:00 P.M. on Aug. 13, 1982 under 150 foot-candle light intensity at Salinas, Calif.

CLASSIFICATION

Botanical: *Chrysanthemum morifolium*, Ramat., cv Vista.

Commercial: Spray anemone pot mum.

INFLORESCENCE

Capitulum:

*Form.*—Semi-incurved to flat.

*Type.*—Anemone.

*Diameter across face.*—35 To 50 mm.

*Corolla of ray florets:*

*Color (general tonality from a distance of three meters).*—Light bronze to golden yellow.

*Color (abaxial).*—Winter: 7C, 7D with light streaking of 168D. Summer: 13B, 13C.

*Color (adaxial).*—Winter: 6D. Summer: 13A.

*Shape.*—Short, oblong, with rounded tip.

Corolla of disc florets:

*Color (mature).*9B.

*Color (immature).*—154B.

Reproductive organs:

*Androecium.*—Present disc florets only; abundant pollen.

*Gynoecium.*—Present both ray and disc florets.

PLANT

General appearance:

*Height.*—Short; 20 to 30 cm. given 2 long day weeks before pinch and lights out, and 1-2 applications 2500 B-9 after lights out.

*Branching pattern.*—Prolific, spreading.

Foliage:

*Color (abaxial).*—147A.

*Color (adaxial).*—147B.

*Shape.*—Deeply lobed. Moderately serrate.

CHART A

COMPARISON OF VISTA AND RITZ

| CULTIVAR | RAY FLORET COLOR | CAPITULUM FORM AND TYPE | BRANCHING PATTERN |
|---|---|---|---|
| VISTA | LIGHT BRONZE TO GOLDEN YELLOW | ANEMONE | SPREADING |
| RITZ | MEDIUM YELLOW | FLAT DAISY | SEMI-SPREADING |

| CULTIVAR | DIAMETER ACROSS FACE OF CAPITULUM | PLANT HEIGHT | FLOWERING RESPONSE PERIOD |
|---|---|---|---|
| VISTA | 35 to 50 mm. | SHORT 20 to 30 cm. | 7 WEEKS |
| RITZ | 70 to 80 mm. | SHORT 25 to 35 cm. | 9 WEEKS |

COMPARISONS MADE OF PLANTS GROWN AS PINCHED, SPRAY POT MUMS IN SALINAS, CALIFORNIA

I claim:

1. A new and distinct cultivar of *Chrysanthemum morifolium,* Ramat., plant known by the cultivar name Vista, as described and illustrated, and particularly characterized as to uniqueness by the combined characteristics of semi-incurved to flat capitulum form; anemone capitulum type; light bronze to golden yellow ray floret color; diameter across face of capitulum ranging from 35 to 50 mm. at maturity; uniform seven weeks flowering response; short plant height, and spreading branching pattern.

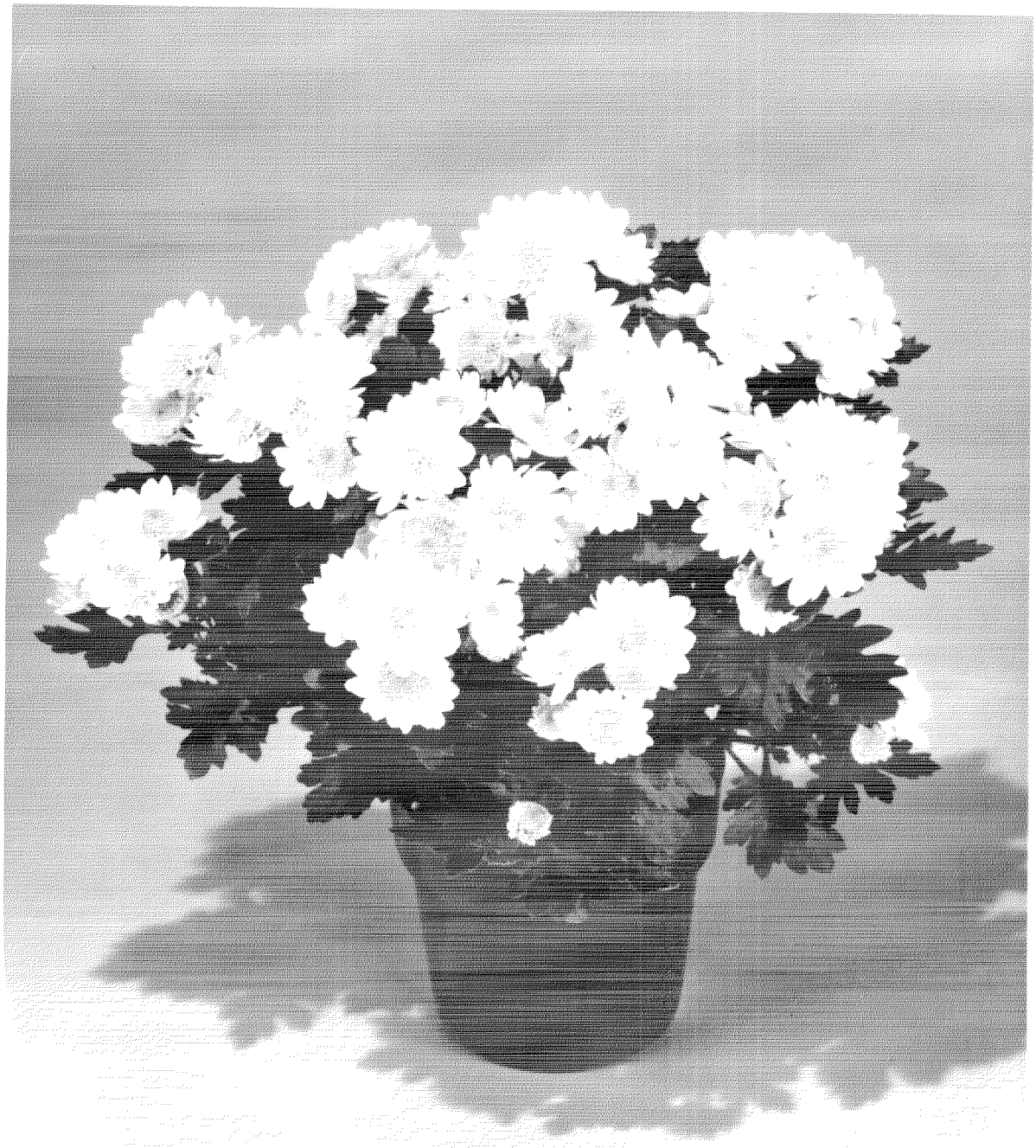

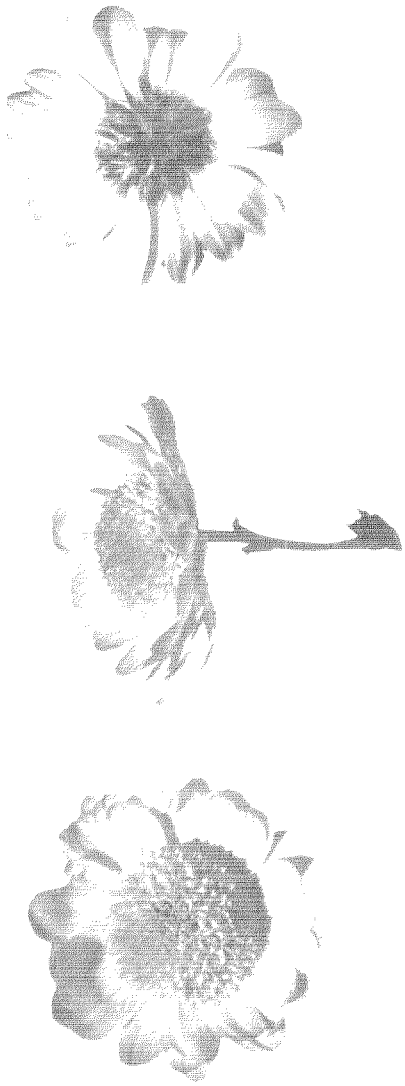

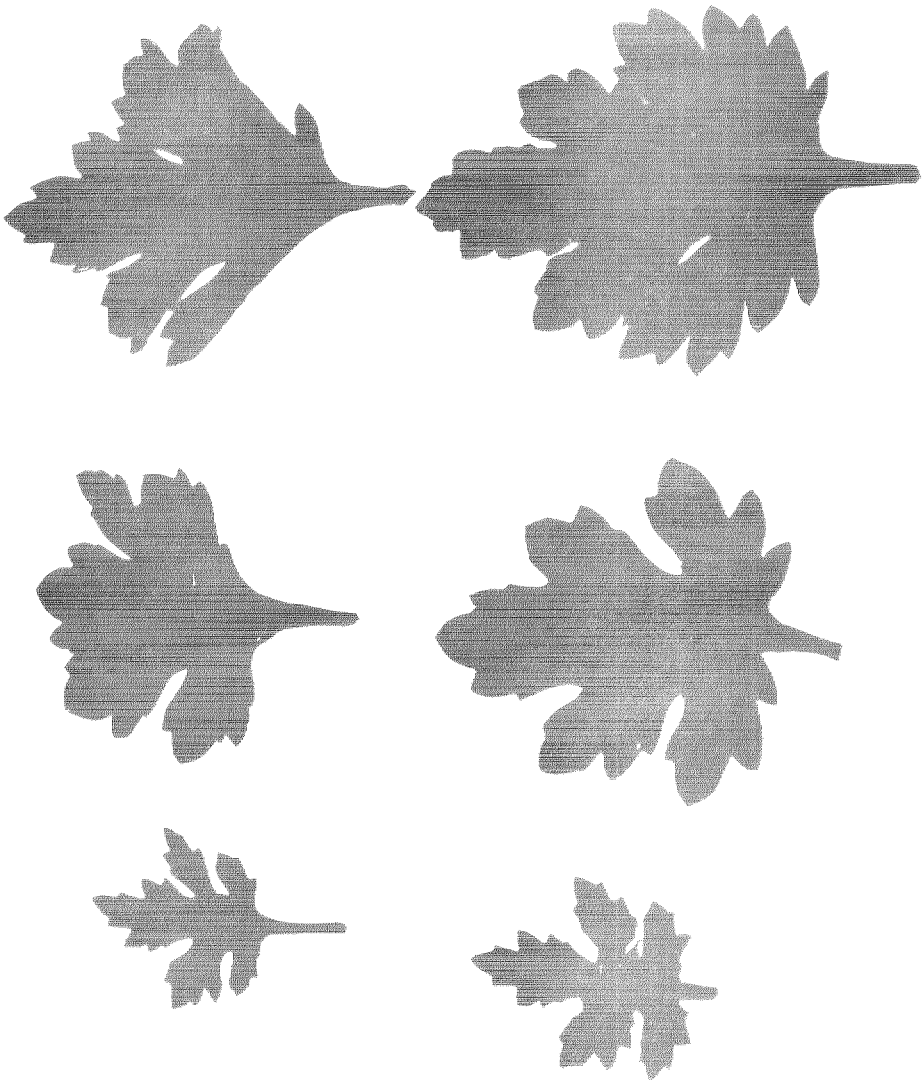

* * * * *